United States Patent [19]
Schütze et al.

[11] Patent Number: 5,104,442
[45] Date of Patent: Apr. 14, 1992

[54] 4,5,6,7-TETRAHYDRO-3-ARYL-INDAZOLES AND THEIR USE AS HERBICIDES

[75] Inventors: Rainer Schütze, Kelkheim; Klaus Bauer, Hanau; Hermann Bieringer, Eppstein/Taunus, all of Fed. Rep. of Germany

[73] Assignee: Hoechst Aktiengesellschaft, Frankfurt am Main, Fed. Rep. of Germany

[21] Appl. No.: 739,687

[22] Filed: Aug. 2, 1991

[30] Foreign Application Priority Data

Aug. 4, 1990 [DE] Fed. Rep. of Germany ....... 4024862

[51] Int. Cl.$^5$ .................... A01N 43/56; C07D 31/56
[52] U.S. Cl. .......................... 71/92; 548/369
[58] Field of Search ............... 548/369; 71/92

[56] References Cited

PUBLICATIONS

Sucrow et al, Chem. Ber., vol. 105 (1972) pp. 2143–2147, 2152.

Primary Examiner—Robert W. Ramsuer
Attorney, Agent, or Firm—Curtis, Morris & Safford

[57] ABSTRACT

The invention relates to novel herbicidal compounds of the formula I or I'

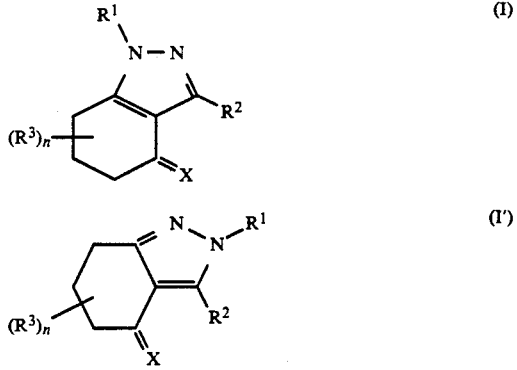

in which
X is an oxygen or sulfur atom,
$R^1$ is H, $C_1$–$C_6$-alkyl, $C_2$–$C_6$-alkenyl, $C_2$–$C_6$-alkynyl, $C_1$–$C_6$-haloalkyl, ($C_1$–$C_4$-alkoxy-$C_1$–$C_4$-alkyl, ($C_1$–$C_6$-alkoxy)carbonyl, aryloxycarbonyl, ($C_1$–$C_6$-alkyl) aminocarbonyl, arylaminocarbonyl, phenyl, substituted phenyl or acyl,
$R^2$ is phenyl or substituted phenyl,
$R^3$ independently of other radicals $R^3$ is H or $C_1$–$C_5$-alkyl and
n is an integer from 0 to 6.

The herbicides are suitable for selectively controlling harmful plants in cereal crops.

19 Claims, No Drawings

4,5,6,7-TETRAHYDRO-3-ARYL-INDAZOLES AND THEIR USE AS HERBICIDES

Tetrahydro-3-aryl-indazoles, process for their preparation, and their use as herbicides.

The invention relates to the technical field of the crop protection agents for selectively controlling broad-leaved weeds and grass weeds in crops of useful plants. The invention relates to 4,5,6,7-tetrahydro-3-aryl-1H-indazoles and -2H-indazoles of the formula I or I',

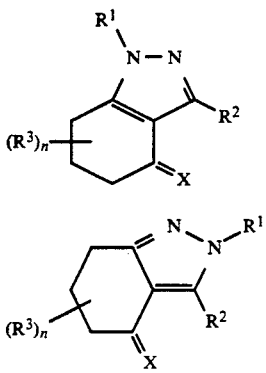

in which
X is an oxygen or sulfur atom,
$R^1$ is H, $C_1$–$C_6$-alkyl, $C_2$–$C_6$-alkenyl, $C_2$–$C_6$-alkynyl, $C_1$–$C_6$-haloalkyl, ($C_1$–$C_4$-alkoxy)-$C_2$–$C_4$-alkyl, ($C_1$–$C_6$-alkoxy)-carbonyl, aryloxycarbonyl, ($C_1$–$C_6$-alkyl)-aminocarbonyl, arylaminocarbonyl, phenyl, substituted phenyl or acyl,
$R^2$ is phenyl or substituted phenyl,
$R^3$ independently of other radicals $R^3$ is H or $C_1$–$C_5$-alkyl and
n is an integer from 0 to 6.

Here and in what follows, the radicals alkyl, alkenyl and alkynyl as well as the alkyl moieties on which the substituted alkyl radicals are based can be straight-chain or branched. Halogen is fluorine, chlorine, bromine or iodine, preferably fluorine or chlorine. Aryl is a carbocyclic or heterocyclic, optionally substituted aromatic ring system, preferably optionally substituted phenyl. Substituted phenyl is preferably phenyl which is substituted by 1 to 5 radicals, in particular 1 to 3 radicals, from the group comprising halogen, alkyl, alkoxy, haloalkyl, haloalkoxy, cyano, nitro, alkanoyl, alkanoylamino, amino, mono- and dialkylamino, carboxyl and derivatives of the carboxyl group, such as alkoxycarbonyl or mono- and dialkylaminocarbonyl. In this context, preferred radicals having carbon chains are those which contain 1 to 6, in particular 1 to 4, carbon atoms. Haloalkyl or haloalkoxy is alkyl or alkoxy, each of which is substituted by one or more atoms from the halogen group. Acyl is a carbonyl group which is bonded to an aliphatic or araliphatic radical or to an aryl radical, preferably alkylcarbonyl.

The compounds according to the invention embrace derivatives of the tetrahydro-1H-indazole and tetrahydro-2H-indazole type, which are regioisomeric compounds. In the processes for their preparation, it happens frequently that the regioisomeric compounds of the formulae I and I' are formed jointly. The compounds of the formula I' are also herbicidally active, but the compounds of the formula I are preferred. Unless specified in greater detail, "compounds according to the invention" in the following text are understood as meaning compounds of the formula I or of the formula I, or mixtures of compounds of the formulae I and I'.

Some compounds of the formula I and I' contain one or more asymmetric carbon atoms or double bonds which are not indicated separately in the formulae I and I'. However, the formulae I and I' embrace all possible stereoisomers which are defined by their specific spatial shape, such as enantiomers, diastereomers and Z- and E-isomers, and which can be obtained from mixtures of stereoisomers by customary methods, or, alternatively, prepared by steroeoselective reactions in combination with the use of stereochemically pure starting materials. Thus, the stereoisomers mentioned, in the pure form as well as their mixtures, are an object of this invention.

Compounds of the formula I or I' according to the invention which are of particular interest are those in which
$R^1$ is H, $C_1$–$C_4$-alkyl, $C$–$C_4$-alkenyl, $C_2$–$C_4$-alkynyl, $C_1$–$C_4$-haloalkyl, ($C_1$–$C_2$-alkoxy)-$C_1$–$C_4$-alkyl, ($C_1$–$C_4$-alkoxy)-carbonyl, ($C_1$–$C_4$-alkyl)aminocarbonyl, phenyloxycarbonyl, phenylaminocarbonyl, phenyl, the 3 last-mentioned groups in each case being unsubstituted or substituted in the phenyl ring by one or more radicals from the group comprising halogen, $C_1$–$C_4$-alkyl, $C_1$–$C_4$-haloalkyl, $C_1$–$C_4$-alkoxy, $C_1$–$C_4$-haloalkoxy, nitro, carboxyl and acid derivatives of carboxyl, in particular $C_1$–$C_4$-alkyl esters, $C_2$–$C_4$-alkenyl esters, $C_2$–$C_4$-alkynyl esters, amide, $C_1$–$C_4$-alkylamide and di-($C_1$–$C_4$-alkyl)amide, or is acyl, in particular $C_1$–$C_6$-alkanoyl.

$R^1$ is preferably H, methyl, ethyl, n- ori-propyl, n-, i-, t- or 2-butyl, allyl, propargyl, trifluoromethyl, 2,2,2-trifluoroethyl, methoxymethyl, ethoxymethyl, 1- and 2-methoxyethyl, 1- and 2-ethoxyethyl, phenyloxycarbonyl, phenylaminocarbonyl, phenyl, the 3 last-mentioned groups in each case being unsubstituted or substituted in the phenyl ring by 1 to 3 radicals from the group comprising halogen, $C_1$–$C_4$-alkyl, trifluoromethyl, $C_1$–$C_4$-alkoxy, nitro, ($C_1$–$C_4$-alkoxy)carbonyl, mono- and di-($C_1$–$C_4$-alkylamino)-carbonyl and $C_2$–$C_3$-alkanoyl, or is formyl or acetyl.

Other compounds of the formula I or I' according to the invention which are of particular interest are those in which
$R^2$ is phenyl which is unsubstituted or substituted by one to three radicals from the group comprising halogen, nitro, $C_1$–$C_4$-alkyl, $C_1$–$C_4$-haloalkyl and $C_1$–$C_4$-alkylsulfonyl.

$R^2$ is preferably phenyl which is substituted by two nonidentical radicals from the group comprising chlorine, nitro, methanesulfonyl and trifluoromethyl.

The radicals $R^3$, independently of one another, are preferably H or methyl; n is preferably 0 to 4, in particular 0 to 3;

X is preferably an oxygen atom.

The invention also relates to a process for the preparation of the compounds of the formula I or I' according to the invention, which comprises reacting
a) compounds of the formula II

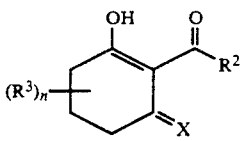

in which $R^2$ and $R^3$ and X are as defined in the above-mentioned formula I or I', with hydrazine derivatives of the formula III

in which $R^1$ is as defined in the abovementioned formula I or I', or, b) in the event that $R^1$=alkyl, compounds of the formula I and I' mentioned, in which $R^1$ is a hydrogen atom, with suitable alkylating agents, or c) with the exception of the preparation of compounds of the formula I', cyclohexane-1,3-diones of the formula IV with chlorohydrazones of the formula V

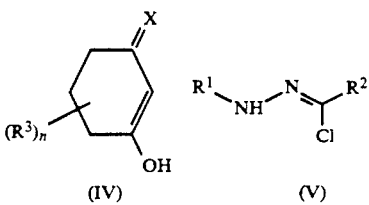

in which $R^1$ to $R^3$ and X are as defined in the formula I or I' mentioned, in the presence of a base, to give compounds of the formula I mentioned.

The reaction of the compound of the formula II by variant a) is preferably carried out in polar, protic (organic) solvents, in particular alcohols, for example methanol, ethanol, propanol, n-butanol, isobutanol, tert.-butanol and 2-butanol, at temperatures from room temperature to the boiling point of the reaction mixture, in particular at reflux temperature.

The alkylating agents by variant b) (cf. equation below) which are suitable for reacting the 1-unsubstituted indazole of the formula I or I'

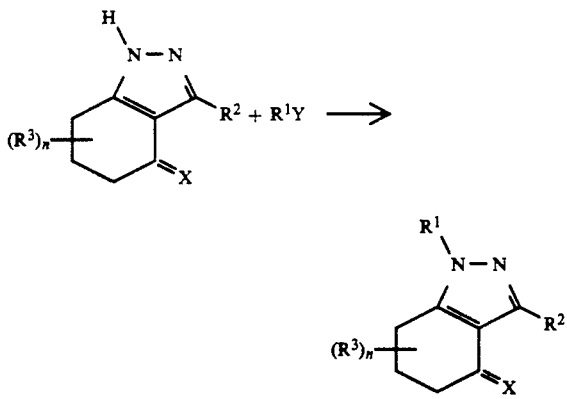

are, for example, customary alkylating agents $R^1Y$ (Y=leaving group) such as dialkyl sulfates, alkyl halides, alkyl methanesulfonates and alkyl p-toluene-sulfonates, and they are employed in the customary manner. For example, a methylation reaction can be carried out using dimethyl sulfate in alkaline solution, preferably in sodium hydroxide solution or alkaline alcohol solution.

In the reaction by variant c), the bicyclic ring system is constructed in the form of a 1,3-dipolar cyclo-addition, and it can be carried out, for example, in aprotic (organic) solvents such as toluene or dioxane as well as in polar, protic (organic) solvents, for example the alcohols methanol and ethanol.

The compounds of the formula II which are required for the preparation of the compounds according to the invention by variant a) can be synthesized by, or in analogy to, processes known from the literature; see, for example, B. J. Chem. Soc. 1953 803, J. Chem. Soc. 1955 341, Tetrahedron Lett. 29, 2491 (1975), J. prakt. Chemie 141, 149 (1934), DE-A-3,902,818, EP-A-249,150, U.S. Pat. No. 4,780,127.

Equally, the hydrazine derivatives III can be prepared by, or in analogy to, methods which are known from the literature; see, for example, J. Am. Chem. Soc. 76, 4869 (1954), Chem. Ber. 81, 81 (1948), J. Chem. Soc. 1958 4723, Org. Synth. 35, 28 (1955), J. Am. Chem. Soc. 80, 5786 (1958), J. Org. Chem. 46, 5413 (1981).

Some of the cyclohexane-1,3-diones of the formula IV are commercially available or can be prepared by known processes; see, for example, J. Chem. Soc. 1953, 811 and Chem. Pharm. Bull. 31, 1518 (1983). The chlorohydrazones of the formula V, which equally act as starting materials for the synthesis of the 1,3-dipolar nitrilimines in variant c), can be prepared by known processes; see, for example, Houben-Weyl Vol. 2, p. 448 and Tetrahedron 17, 3 (1962).

In the reaction by variants a) and b), regioisomeric compounds, in particular, can be formed.

The compounds of the formula I or I' according to the invention have an excellent herbicidal activity against a broad range of economically important monocotyledon and dicotyledon harmful plants. The active substances also act efficiently on perennial weeds which produce shoots from rhizomes, rootstocks or other perennial organs and which are difficult to control. In this context, it does not matter whether the substances are applied pre-sowing, pre-emergence or post-emergence. Specifically, examples may be mentioned of some representatives of the monocotyledon and dicotyledon weed flora which can be controlled by the compounds according to the invention, without the enumeration being a restriction to certain species.

Examples of weed species on which the active substance acts efficiently are, from amongst the monocotyledons, Avena, Lolium, Alopecurus, Phalaris, Echinochloa, Digitaria, Setaria et cetera, and also Cyperus species from the annual sector, and from amongst the perennial species Agropyron, Cynodon, Imperata and Sorghum et cetera, and also perennial Cyperus species.

In the case of the dicotyledon weed species, the range of action extends to species such as, for example, Galium, Viola, Veronica, Lamium, Stellaria, Amaranthus, Sinapis, Ipomoea, Matricaria, Abutilon, Sida et cetera from amongst the annuals, and Convolvulus, Cirsium, Rumex, Artemisia et cetera in the case of the perennial weeds.

The active substances according to the invention also effect outstanding control of weeds which occur under the specific conditions of rice growing, such as, for example, Sagittaria, Alisma, Eleocharis, Scirpus, Cyperus, et cetera.

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active substances are applied post-emergence to the green parts of the plants, growth equally stops drastically a very short time after the treatment and the weed plants remain at the growth stage of the point of time of application, or they die more or less quickly after a certain time, so that in this manner competition by the weeds, which is harmful to the crop plants, is eliminated at a very early point in time and in a sustained manner by using the compounds of the formula I according to the invention.

Even though the compounds according to the invention have an excellent herbicidal activity against monocotyledon and dicotyledon weeds, crop plants of economically important crops, such as, for example, wheat, barley, rye, rice, maize, sugar beet, cotton and soya, are damaged not at all, or only to a negligible extent. For these reasons, the present compounds are highly suitable for selectively controlling undesired plant growth in plantings for agricultural use.

The compounds according to the invention can be formulated in many ways, depending on the biological and/or chemio-physical parameters which prevail. The following are examples of suitable formulation possibilities: wettable powders (WP), water-soluble powders (SP), water-soluble concentrates (SL), emulsifiable concentrates EC), emulsions (EW) such as oil-in-water and water-in-oil emulsions, sprayable solutions or emulsions, suspension concentrates (SC), dispersions on an oil or water base, oil-miscible solutions (OL), suspoemulsions, capsule suspensions (CS), dusting powders DP), seed-dressing agents, granules for soil application or for broadcasting, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie [Chemical Technology]" Volume 7, G. Hauser Verlag Munich, 4th Edition 1986; Van Valkenburg, "Pesticides Formulations", Marcel Dekker N.Y. 1973; K Martens, "Spray Drying Handbook", 3rd Ed. 1979, G. Goodwin Ltd. London.

The formulation auxiliaries which are necessary such as inert materials, surfactants, solvents and further additives are equally known and are described, for example, in: Watkins, "Handbook of Insecticide Dust Diluents and Carriers", 2nd Ed., Darland Books, Galdwell N. J.; H. v. Olphen, "Introduction to Clay Colloid Chemistry"; 2nd Ed., J. Wiley & Sons, N.Y.; Marsden, "Solvents Guide", 2nd Ed., Interscience, N.Y. 1950; McCutcheon's "Detergents and Emulsifiers Annual", MG Publ. Corp., Ridgewood N.J.; Sisley and Wood, "Encyclopedia of Surface Active Agents", Chem. Publ. Co. Inc., N.Y 1964; Schönfeldt, "Grenzflächenaktive Äthylenoxidaddukte [Surface-active Ethylene Oxide Adducts]", Wiss. Verlagsgesell., Stuttgart 1976; Winnacker-Küchler, "Chemische Technologie [Chemical Technology]", Volume 7, G. Hauser Verlag Munich, 4th Edition 1986.

On the basis of these formulations, it is also possible to prepare combinations with other pesticidally active substances, fertilizers and/or growth regulators, for example in the form of a readymix or as a tank mix.

Wettable powders are preparations which are uniformly dispersible in water and which contain, besides a diluent or inert substance, wetting agents, for example polyoxyethylated alkylphenols, polyoxyethylated fatty alcohols and fatty amines, fatty alcohol polyglycol ether sulfates, alkanesulfonates or alkylarylsulfonates, and dispersing agents, for example sodium ligninsulfonate, sodium 2,2,-dinaphthylmethane-6,6,-disulfonate, sodium dibutylnaphthalene sulfonate or, alternatively, sodium oleylmethyltaurinate, in addition to the active substance.

Emulsifiable concentrates are prepared by dissolving the active substance in an organic solvent, for example butanol, cyclohexanone, dimethylformamide, xylene, or, alternatively, higher-boiling aromatics or hydrocarbons, with the addition of one or more emulsifiers. The following are examples of emulsifiers which can be used: calcium alkylarylsulfonates such as Ca dodecylbenzenesulfonate, or non-ionic emulsifiers such as fatty acid polyglycol esters, alkylaryl polyglycol ethers, fatty alcohol polyglycol ethers, propylene oxide/ethylene oxide condensation products (for example block copolymers), alkyl polyglycol ethers, sorbitan fatty acid esters, polyoxyethylene sorbitan fatty acid esters or polyoxyethylene sorbitol esters.

Dusts are obtained by grinding the active substance with finely divided solid substances, for example talc, natural clays such as kaolin, bentonite and pyrophillite, or diatomaceous earth.

Granules can be prepared either by spraying the active substance onto adsorbent, granulated inert material, or by applying active substance concentrates by means of tackifiers, for example polyvinyl alcohol, sodium polyacrylate or, alternatively, mineral oils, to the surface of carriers such as sand, kaolinites or of granulated inert material. Suitable active substances can also be granulated in the fashion customary in the manufacture of fertilizer granules, if desired as a mixture with fertilizers.

Disk granules, fluidized-bed granules, extruder granules and spray granules can be prepared by customary processes; see, for example, processes in "Spray Drying Handbook", 3rd Ed. 1979, G. Goodwin Ltd., London; J. E. Browning, "Agglomeration", Chemical and Engineering 1967, pages 147 et seq; "Perry's Chemical Engineer's Handbook", 5th Ed., McGraw-Hill, New York 1973, p. 8–57.

For further information on the formulation of crop protection agents see, for example, G. G. Klingman, "Weed Control as a Science", John Wiley and Sons, Inc., New York, 1961, pages 81–96 and J. D. Freyer's A. Evans, "Weed Control Handbook", 5th Ed., Blackwell Scientific Publications, Oxford, 1968, pages 101–103.

As a rule, the agrochemical preparations contain 0.1 to 99 percent in particular 0.1 to 95% by weight, of herbicidal active substance.

In wettable powders, the active substance concentration is, for example, about 10 to 90% by weight, the remainder to 100% by weight is composed of customary formulation components. In the case of emulsifiable concentrates, the active substance concentration can be about 1 to 80% by weight. Formulations in the form of dusts usually contain 1 to 20% by weight of active substance, sprayable solutions about 0.2 to 20% by weight. In the case of granules, the active substance content depends partly on whether the active substance is liquid or solid. The content in the water-dispersible granules is usually between 10 and 90% by weight.

In addition, the active substance formulations mentioned may contain the adhesives, wetting agents, dispersing agents, emulsifiers, penetrants, solvents, fillers or carriers which are customary in each case.

For use, the formulations which are in commercially available form may be diluted in the customary fashion, for example by means of water in the case of wettable powders, emulsifiable concentrates, dispersions and water-dispersible granules. Formulations in the form of dusts, soil granules or granules for broadcasting, as well as sprayable solutions, are usually not diluted any further with other inert substances before use.

The application rate required, of the compounds according to the invention, varies with the external conditions such as temperature, humidity, the nature of the herbicide used, et cetera. It can vary within wide limits, for example between 0.001 and 10.0 kg/ha or more of active ingredient, but it is preferably between 0.005 and 5 kg/ha.

Mixtures or mixed formulations with other active substances such as, for example, insecticides, acaricides, herbicides, safeners, fertilizers, growth regulators or fungicides, may also be possible.

The following examples are intended to illustrate the invention:

A) FORMULATION EXAMPLES a) A dust is obtained by mixing 10 parts by weight of a compound of the formula (I) and 90 parts by weight of talc as inert substance, and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium ligninsulfonate and 1 part by weight of sodium oleoylmethyl taurinate as wetting and dispersing agent, and grinding the mixture in a pinned-disk mill.

c) A dispersion concentrate which is readily dispersible in water is obtained by mixing 20 parts by weight of a compound of the formula (I) with 6 parts by weight of alkylphenol polyglycol ether ((R)Triton X 207), 3 parts by weight of isotridecanol polyglycol ether (8 EO) and 71 parts by weight of paraffinic mineral oil (boiling range for example approx. 255° to above 277° C.), and grinding the mixture in a ball mill to a fineness of below 5 micron.

d) An emulsifiable is obtained from 15 parts by weight of a compound of the formula (I), 75 parts by weight of cyclohexane as solvent and 10 parts by weight of oxyethylated nonylphenol as emulsifier.

e) Water-dispersible granules are obtained by mixing 75 parts by weight of a compound of the formula (I),
10 parts by weight of calcium ligninsulfonate,
5 parts by weight of sodium lauryl sulfate,
3 parts by weight of polyvinyl alcohol and
7 parts by weight of kaolin, grinding the mixture on a pinned-disk mill, and granulating the powder in a fluidized bed by spraying on water as the granulation liquid.

f) Water-dispersible granules are also obtained by homogenizing and precomminuting 25 parts by weight of a compound of the formula (I),
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water on a colloid mill, subsequently grinding the mixture on a bead mill, and atomizing and drying the resulting suspension in a spray tower by means of a single-fluid jet.

g) Extruder granules are obtained by mixing 20 parts by weight of active substance of the formula (I), 3 parts by weight of sodium ligninsulfonate, 1 part by weight of carboxymethylcellulose and 76 parts by weight of kaolin, grinding the mixture and moistening it with water. This mixture is extruded and subsequently dried in a stream of air.

h) Formulations with compounds of the formula I' are obtained analogously to the above Examples a) to g) when these latter compounds are employed in the place of compounds of the formula I.

B) PREPARATION EXAMPLES 4,5,6,7-Tetrahydro-4-oxo-3-(2-nitro-phenyl)-1H-indazole (to Example 1, Table 1)

3.2 g (12.2 mmol) of 2-nitrobenzoylcyclohexane-1,3-dione and 0.52 g (12.2 mmol) of hydrazine hydrate (80%) are refluxed for 4 hours in 120 ml of ethanol. The ethanol is subsequently distilled off under reduced pressure, and 80 ml of methanol are added. The solid which precipitates is filtered off with suction and dried in vacuo. 1.41 g (45% of theory) of 4,5,6,7-tetrahydro-4-oxo-3-(2-nitro-phenyl)-1H-indazole of the formula

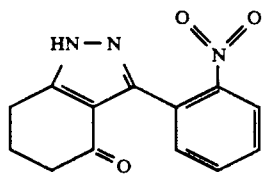

and of melting point 236° C. (decomp.) are obtained.

4,5,6,7-Tetrahydro-4-oxo-3-(4-chloro-2-nitrophenyl)-1-ethyl-1H-indazole (to Example 2, Table 1)

2.08 g (7.13 mmol) of 4,5,6,7-tetrahydro-4-oxo-3-(4-chloro-2-nitrophenyl)-1H-indazole are dissolved in 80 ml of 10% aqueous sodium hydroxide solution, insolubles are filtered off, and 1.2 g (7.8 mmol) of diethyl sulfate are then added to the solution. Stirring is subsequently continued for 1.5 hours at room temperature and for 1 hour at 0° C., during which process a precipitate starts to separate out after as early as approx. 10 minutes. When the reaction is complete, the precipitate is filtered off with suction and chromatographed on silica gel using ethyl acetate/dichloromethane (1:2). The fraction of $R_f = 0.72$ contains 0.34 g (15.3% of theory) of the desired product of the formula

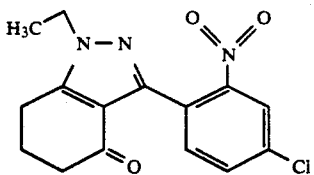

and of melting point 184° C.

4,5,6,7-Tetrahydro-4-oxo-1,3-diphenyl-1H-indazole (to Example 4, Table 1)

3 g of benzophenylhydrazide chloride together with 5.84 g of cyclohexane-1,3-dione are dissolved in 80 ml of toluene, and 1.4 g of triethylamine are added. The solution is heated to 80°–90° C. for 4 hours. It is subsequently allowed to cool to room temperature and washed with 1 N HCl and then with a sodium hydrogen carbonate solution. The organic phase is dried, and the toluene is stripped off under reduced pressure. The residue is taken up in methanol and allowed to crystallize slowly. In this manner, 1.3 g (35% of theory) of the desired product of the formula

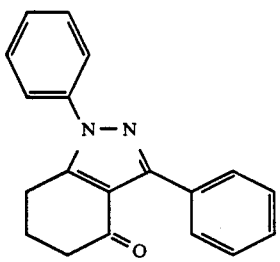

of melting point 162° C. are obtained.

4,5,6,7-Tetrahydro-4-oxo-1-methyl-3-(2-chloro-4-methane-sulfonylphenyl)-1H-indazole (to Example 6, Table 1)

2 g of 2-(2-chloro-4-methanesulfonylbenzoyl)cyclohexane-1,3-dione are dissolved in 50 ml of ethanol, 0.28 g of methylhydrazine are added, and the solution is then refluxed for 4 hours. It is subsequently allowed to cool, and the precipitate which has separated out is filtered off with suction. 0.85 g (41% of theory) of the desired product of the formula

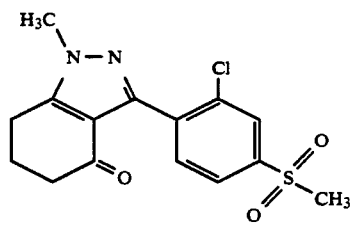

of melting point 208° C. is obtained.

Table 1 which follows lists Examples 1, 2, 4 and 6 together with further examples of the formula VI which are obtained in an analogous manner:

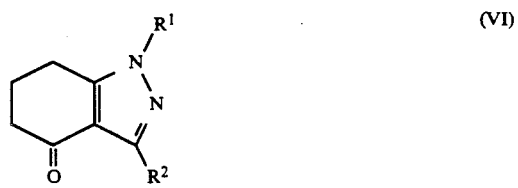

(VI)

TABLE 1

| Example | R² | R¹ | M.P. [°C.] |
|---|---|---|---|
| 1 | 2-nitrophenyl | H | 236 |
| 2 | 2-nitro-4-chlorophenyl | C₂H₅ | 184 |
| 3 | 2-nitrophenyl | phenyl | 221 |
| 4 | phenyl | phenyl | 162 |

TABLE 1-continued
| Example | R² | R¹ | M.P. [°C.] |
|---|---|---|---|
| 5 | 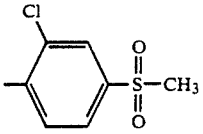 |  | 115–118 |
| 6 | 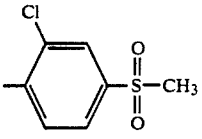 | CH₃ | 208 |
| 7 | 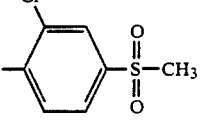 | H | 222 |
| 8 | 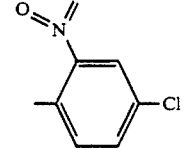 | H | 242 |
| 9 | 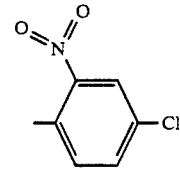 | 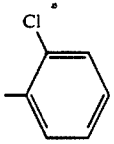 | 138–141 |
| 10 | 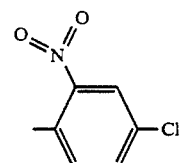 | 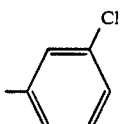 | 128 |
| 11 | 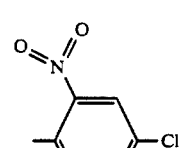 | 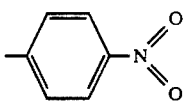 | 100–103 |
| 12 | 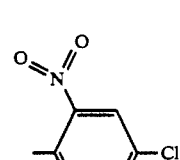 | 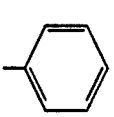 | 85 |
| 13 | 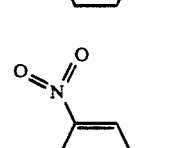 | CH₃ | 215 |

TABLE 1-continued

| Example | R² | R¹ | M.P. [°C.] |
|---|---|---|---|
| 14 | 2,4-dichlorophenyl (Cl at 2 and 4 positions) | phenyl | 154 |
| 15 | 2-nitro-3,6-dimethylphenyl (NO₂, CH₃, CH₃) | phenyl | 193 |
| 16 | 2-nitro-3,6-dimethylphenyl | H | 213 |
| 17 | 2-chloro-4-fluorophenyl | H | 191 |
| 18 | 2-methyl-4-nitrophenyl | CH₃ | 213 |
| 19 | 2-chloro-4-nitrophenyl | CH₃—C=O | 131 |
| 20 | 3-methyl-4-nitrophenyl | CH₃ | 175 |
| 21 | 2-nitro-4-chlorophenyl | CH₂—CF₃ | 182 |
| 22 | 2-nitro-4-chlorophenyl | t.C₄H₉ | 250 |
| 23 | 2-nitro-4-chlorophenyl | n.C₃H₇ | 144–148 (mixture of isomers) |

TABLE 1-continued

| Example | R² | R¹ | M.P. [°C.] |
|---|---|---|---|
| 24 | 4-chloro-2-nitrophenyl (methyl) | n.-C₄H₉ | |
| 25 | 2-nitrophenyl (methyl) | CH₃ | |
| 26 | 2-nitrophenyl (methyl) | C₂H₅ | |
| 27 | 2-nitrophenyl (methyl) | CH₂CF₃ | |
| 28 | 2-nitrophenyl (methyl) | t.C₄H₉ | |
| 29 | 2-nitrophenyl (methyl) | n.C₃H₇ | |
| 30 | 2-nitrophenyl (methyl) | n.C₄H₉ | |
| 31 | 2-chloro-4-(methylsulfonyl)phenyl (methyl) | CH₂CF₃ | 95 (mixture of isomers) |
| 32 | 2-chloro-4-(methylsulfonyl)phenyl (methyl) | C₂H₅ | |

TABLE 1-continued
| Example | R² | R¹ | M.P. [°C.] |
|---|---|---|---|
| 33 | 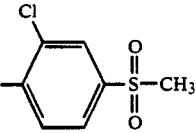 | t.C₄H₉ | |
| 34 | 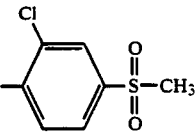 | n.C₃H₇ | |
| 35 | 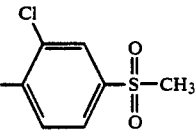 | n.C₄H₉ | |
| 36 | 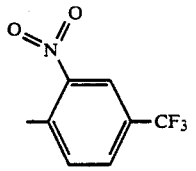 |  | 79 |
| 37 | 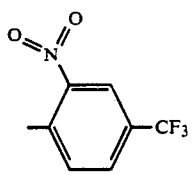 | CH₃ | 168 |
| 38 | 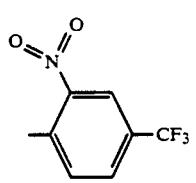 | H | 214 |
| 39 | 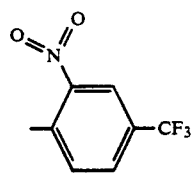 | CH₂CF₃ | |
| 40 | 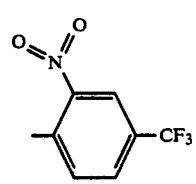 | C₂H₅ | |
| 41 | 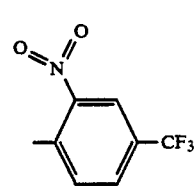 | t.C₄H₉ | |

TABLE 1-continued

| Example | R² | R¹ | M.P. [°C.] |
|---|---|---|---|
| 42 | 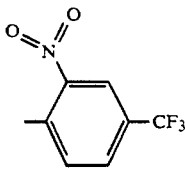 2-nitro-4-trifluoromethylphenyl (attached via methyl) | C₃H₇ | |
| 43 | 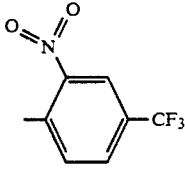 2-nitro-4-trifluoromethylphenyl (attached via methyl) | n-C₄H₉ | |
| 44 | 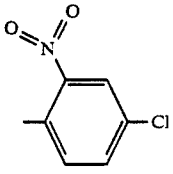 2-nitro-4-chlorophenyl (attached via methyl) | —CO—CH₃ | 222 |
| 45 | " | —CO—OC₂H₅ | 138 |
| 46 | " | —CO—NH—C₂H₅ | 192 |
| 47 | " | —CO—NH-i-C₃H₇ | 188 |
| 48 | " | 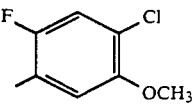 2-chloro-4-fluoro-5-methoxyphenyl | 92–95 |
| 49 | " | —CO—H | 183 |
| 50 | " | —CO—O—C₆H₅ | 261 |
| 51 | " | 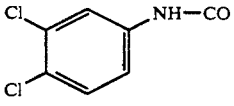 3,4-dichlorophenyl-NH—CO | 216–218 |
| 52 | —C₆H₅ | —CH₃ | 105 |
| 53a | 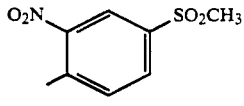 2-nitro-4-methylsulfonylphenyl (attached via methyl) | —CH₃ | |
| 53b | 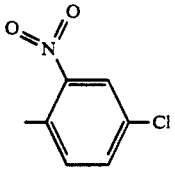 2-nitro-4-chlorophenyl (attached via methyl) | —CO—NH-t-C₄H₉ | 175 |
| 53c | 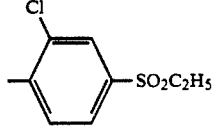 2-chloro-4-ethylsulfonylphenyl (attached via methyl) | H | 226 |
| 53d | " | CH₃ | 75–81 (mixture of isomers) |

TABLE 1-continued

| Example | R² | R¹ | M.P. [°C.] |
|---|---|---|---|
| 53e | 3-Cl, 4-SO₂CH₃-phenyl | 4-chlorophenyl | 168–175 |

The compounds of the formula VII which are listed in Table 2 below are obtained analogously to the compounds in Table 1 above:

TABLE 2

(VII)

| Example | R² | R¹ | $R_a^3$ | $R_b^3$ | $R_c^3$ | $R_d^3$ | $R_e^3$ | $R_f^3$ | M.P. [°C.] |
|---|---|---|---|---|---|---|---|---|---|
| 54 | 2-NO₂, 4-Cl-phenyl | CH₃ | H | H | H | H | CH₃ | CH₃ | 132 |
| 55 | 2-NO₂, 4-Cl-phenyl | CH₃ | CH₃ | H | H | H | CH₃ | CH₃ | |
| 56 | 2-Cl, 4-SO₂CH₃-phenyl | CH₃ | H | H | H | H | CH₃ | CH₃ | 170–175 (mixture of isomers) |
| 57 | 2-Cl, 4-SO₂CH₃-phenyl | CH₃ | CH₃ | H | H | H | CH₃ | CH₃ | 182–190 |
| 58 | 2-Cl, 4-SO₂CH₃-phenyl | H | H | H | CH₃ | CH₃ | H | H | |
| 59 | 2-Cl, 4-SO₂CH₃-phenyl | CH₃ | H | H | CH₃ | CH₃ | H | H | |
| 60 | 2-Cl, 4-SO₂CH₃-phenyl | Ph | H | H | CH₃ | CH₃ | H | H | |

TABLE 2-continued

Structure (VII): 6-membered ring with Ra³, Rb³ at one carbon; Rc³, Rd³ at next; Re³, Rf³ at next; carbonyl (=O); fused to pyrazole with N-R¹, N, and C-R²

| Example | R² | R¹ | Ra³ | Rb³ | Rc³ | Rd³ | Re³ | Rf³ | M.P. [°C] |
|---|---|---|---|---|---|---|---|---|---|
| 61 | 2-Cl-4-(SO₂CH₃)-phenyl | t.C₄H₉ | H | H | CH₃ | CH₃ | H | H | |
| 62 | 2-NO₂-4-Cl-phenyl | H | H | H | H | H | CH₃ | CH₃ | |
| 63 | 2-NO₂-4-Cl-phenyl | H | CH₃ | H | H | H | CH₃ | CH₃ | |
| 64 | 2-Cl-4-(SO₂CH₃)-phenyl | H | H | H | H | H | CH₃ | CH₃ | |
| 65 | 2-Cl-4-(SO₂CH₃)-phenyl | H | CH₃ | H | H | H | CH₃ | CH₃ | |
| 66 | 2-Cl-4-(SO₂CH₃)-phenyl | Ph | H | H | H | H | CH₃ | CH₃ | |
| 67 | 2-NO₂-4-Cl-phenyl | i.C₃H₇ | H | H | CH₃ | CH₃ | H | H | |
| 68 | 2-NO₂-4-Cl-phenyl | C₂H₅ | H | H | CH₃ | CH₃ | H | H | |
| 69 | 2-Cl-4-(SO₂CH₃)-phenyl | C₂H₅ | H | H | CH₃ | CH₃ | H | H | |

TABLE 2-continued
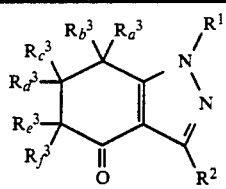
(VII)
| Example | R² | R¹ | $R_a^3$ | $R_b^3$ | $R_c^3$ | $R_d^3$ | $R_e^3$ | $R_f^3$ | M.P. [°C.] |
|---|---|---|---|---|---|---|---|---|---|
| 70 | 2-Cl-4-(SO₂CH₃)-phenyl | n.C₃H₇ | H | H | CH₃ | CH₃ | H | H | |
| 71 | 2-NO₂-4-Cl-phenyl | H | H | H | CH₃ | CH₃ | H | H | 231 |
| 72 | 2-NO₂-4-Cl-phenyl | CH₃ | H | H | CH₃ | CH₃ | H | H | 158–165 |
| 73 | 2-NO₂-4-Cl-phenyl | Ph | H | H | CH₃ | CH₃ | H | H | |
| 74 | 2-NO₂-4-Cl-phenyl | t.C₄H₉ | H | H | CH₃ | CH₃ | H | H | |
| 75 | 2-NO₂-4-Cl-phenyl | n.C₃H₇ | H | H | CH₃ | CH₃ | H | H | |
| 76 | 2-NO₂-4-CF₃-phenyl | H | H | H | CH₃ | CH₃ | H | H | |
| 77 | 2-NO₂-4-CF₃-phenyl | CH₃ | H | H | CH₃ | CH₃ | H | H | |

TABLE 2-continued (VII)

[Structure: cyclohexenone fused with pyrazole ring, showing $R_a^3$, $R_b^3$, $R_c^3$, $R_d^3$, $R_e^3$, $R_f^3$ substituents on the ring, $R^1$ on nitrogen, $R^2$ on the exocyclic CH group, with C=O]

| Example | R² | R¹ | $R_a^3$ | $R_b^3$ | $R_c^3$ | $R_d^3$ | $R_e^3$ | $R_f^3$ | M.P. [°C] |
|---------|----|----|---------|---------|---------|---------|---------|---------|-----------|
| 78 | 2-NO₂-4-CF₃-phenyl | Ph | H | H | CH₃ | CH₃ | H | H | |
| 79 | 2-NO₂-4-CF₃-phenyl | C₂H₅ | H | H | CH₃ | CH₃ | H | H | |
| 80 | 2-NO₂-4-CF₃-phenyl | t.C₄H₉ | H | H | CH₃ | CH₃ | H | H | |
| 81 | 2-NO₂-4-Cl-5-methylphenyl | C₂H₅OCO | H | H | CH₃ | CH₃ | H | H | 116 |
| 82 | " | CH₃CO | H | H | CH₃ | CH₃ | H | H | 170 |
| 83 | " | C₆H₅OCO | H | H | CH₃ | CH₃ | H | H | 176 |
| 84 | " | C₂H₅NHCO | H | H | CH₃ | CH₃ | H | H | 200 |
| 85 | " | i-C₃H₇NHCO | H | H | CH₃ | CH₃ | H | H | 204 |
| 86 | " | H—CO | H | H | CH₃ | CH₃ | H | H | 162 |
| 87 | " | CH₂CF₃ | H | H | CH₃ | CH₃ | H | H | 115 |

C) Biological Examples

The damage to the weed plants, or the tolerance by the crop plants, was scored using a key in which the effectiveness is expressed by figures from 0–5. The figures denote:

0 = no effect or damage
1 = 0 to 20% effect or damage
2 = 20 to 40% effect or damage
3 = 40 to 60% effect or damage
4 = 60 to 80% effect or damage
5 = 80 to 100% effect or damage 1. Pre-emergence effect on weeds Seeds or rhizome pieces of monocotyledon and dicotyledon weed plants were placed in sandy loam soil in plastic pots and covered with soil. The compounds according to the invention which were formulated in the form of wettable powders or emulsion concentrates were then applied to the surface of the soil cover in the form of aqueous suspensions or emulsions at an application rate of 600 to 800 l of water/ha (converted), in various dosages.

After the treatment, the pots were placed in a greenhouse and kept under good growth conditions for the weeds. After the test plants had emerged, the damage to the plants or the negative effect on the emergence was scored visually after a test period of 3 to 4 weeks by comparison with untreated controls. As shown by the score figures in Table 3, the compounds according to the invention have a good herbicidal pre-emergence action against a broad range of grass weeds and broad-leaved weeds.

TABLE 3

Pre-emergence effect

| | Dosage rate | Herbicidal action | | | |
|---------|-------------|------|------|------|------|
| Example | (kg of a.i./ha) | SIAL | CRSE | STME | ECCR |
| 5 | 1.25 | 3 | 5 | 5 | 5 |
| 1 | 1.25 | 3 | 4 | 5 | 5 |
| 8 | 1.25 | 5 | 4 | 5 | 3 |
| 13 | 1.25 | 5 | 5 | 5 | 5 |
| 15 | 1.25 | No effect | | | |

Abbreviations:
SIAL = Sinapis alba
CRSE = Chrysanthemum segetum
STME = Stellaria media
ECCR = Echinochloa crus-galli
a.i. = Active substance

2. Post-emergence effect on weeds

Seeds or rhizome pieces of monocotyledon and dicotyledon weeds were placed in sandy loam soil in plastic pots, covered with soil and grown in a greenhouse under good growth conditions. Three weeks after sowing, the test plants were treated in the three-leaf stage.

The compounds according to the invention which were formulated as wettable powders or as emulsion concentrates were sprayed in various dosages on the green parts of the plants at an application rate of 600 to 800 1 of water/ha (converted) and, after the test plants had remained in the greenhouse for about 3–4 weeks under ideal growth conditions, the effect of the preparations was scored visually by comparison with untreated controls. The agents according to the invention also have a good herbicidal post-emergence action against a broad range of economically important grass weeds and broad-leaved weeds (Table 4).

TABLE 4

| | | Post-emergence effect | | | |
| | Dosage rate | Herbicidal action | | | |
| Example | (kg of a.i./ha) | SIAL | CRSE | STME | ECCR |
|---|---|---|---|---|---|
| 5 | 1.25 | 4 | 2 | 5 | 1 |
| 1 | 1.25 | 3 | 1 | 2 | 1 |
| 8 | 1.25 | 4 | 2 | 4 | 3 |
| 13 | 1.25 | 5 | 1 | 5 | 3 |
| 15 | 1.25 | 4 | 0 | 4 | 1 |

Abbreviations:
SIAL = *Sinapis alba*
CRSE = *Chrysanthemum segetum*
STME = *Stellaria media*
ECCR = *Echinochloa crus-galli*
a.i. = Active substance

3. Tolerance by crop plants

In further greenhouse experiments, seeds of a substantial number of crop plants and weeds were placed in sandy loam soil and covered with soil. Some of the pots were treated immediately as described under 1., and the remaining pots were placed in a greenhouse until the plants had developed two to three true leaves and then sprayed with various dosages f the substances according to the invention, as described under 2.

Visual scoring four to five weeks after the application and after the plants had been in the greenhouse revealed that the compounds according to the invention did not inflict any damage to dicotyledon crops such as, for example, soya, cotton, oilseed rape, sugar beet and potatoes when used pre- and post-emergence, even when high dosages of active substance were used. Moreover, some substances also left Gramineae crops such as, for example, barley, wheat, rye, Sorghum species, maize or rice unharmed. The compounds according to the invention therefore have a high selectivity when used for controlling undesired plant growth in agricultural crops.

4. Herbicidal effect when used in rice

In sealed plastic pots, tubers and rhizomes, or young plants or seeds, of various rice weeds such as Cyperus species, Eleocharis, Scirpus and Echinochloa were placed or planted in specific rice soil which was then water-logged up to 1 cm above the soil. Rice plants underwent the same treatment.

In the pre-emergence method, i.e. 3–4 days after transplanting, the compounds according to the invention were poured into the built-up water in the form of aqueous suspensions or emulsions or sprinkled into the water in the form of granules.

Three weeks later, the herbicidal effect and any damage to rice was scored visually in each case. The results show that the compounds according to the invention are suitable for selectively controlling weeds in rice. In comparison with previous rice herbicides, the compounds according to the invention are distinguished by the fact that they effectively control a large number of weeds, in particular also those which germinate from perennial organs and which are difficult to control, while being tolerated by rice.

We claim:

1. A compound of the formula I or I',

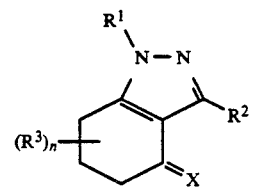

(I)

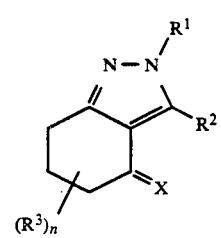

(I')

in which

X is oxygen or sulfur;

$R^1$ is H, $C_1$-$C_6$-alkyl, $C_2$-$C_6$-alkenyl, $C_2$-$C_6$-alkynyl, $C_1$-$C_6$-haloalkyl, ($C_1$-$C_4$-alkoxy)-$C_1$-$C_4$-alkyl, ($C_1$-$C_6$-alkoxy)carbonyl, aryloxycarbonyl, ($C_1$-$C_6$-alkyl)aminocarbonyl, ($C_1$-$C_6$-alkyl)aminocarbonyl, arylaminocarbonyl, phenyl, substituted phenyl or acyl;

$R^2$ is nitrophenyl or nitrophenyl substituted by one or two radicals from the group consisting of halogen, nitro, $C_1$-$C_4$-alkyl, $C_1$-$C_4$-haloalkyl and $C_1$-$C_4$-alkylsulfonyl;

$R^3$ independent of each of the $R^3$ radicals is H or $C_1$-$C_5$-alkyl; and n is an integer from 0 to 6; and with the exception of 4,5,6,7-tetrahydro-4-oxo-1,6,6-trimethyl-3-(4-nitrophenyl)-1H-indazole.

2. The compound claimed in claim 1, wherein:

$R^1$ is H, $C_{-C_4}$-alkyl, $C_2$-$C_4$-alkenyl, $C_2$-$C_4$-alkynyl, $C_1$-$C_4$-haloalkyl, ($C_1$-$C_2$-alkoxy)-$C_1$-$C_4$-alkyl, ($C_1$-$C_4$-alkoxy)-carbonyl, ($C_1$-$C_4$-alkyl)aminocarbonyl, acyl, phenyloxycarbonyl, phenylaminocarbonyl, or phenyl, each of the phenyloxycarbonyl, phenylaminocarbonyl or phenyl groups being unsubstituted or substituted in the phenyl ring by one or more halogen, $C_1$-$C_4$-alkyl, $C_1$-$C_4$-haloalkyl, $C_1$-$C_4$-alkoxy, $C_1$-$C_4$-haloalkoxy, nitro, carboxyl or carboxyl derivatives.

3. The compound claimed in claim 1, wherein:

$R^1$ is H, methyl, ethyl, n- or i-propyl, n-, i-, t- or 2-butyl, allyl, propargyl, trifluoromethyl, 2,2,2-trifluoroethyl, methoxymethyl, ethoxymethyl, 1- and 2-methoxyethyl, 1- and 2-ethoxyethyl, formyl, acetyl, phenyloxycarbonyl, phenylaminocarbonyl, or phenyl, each of the phenyloxycarbonyl, phenylaminocarbonyl or phenyl groups being unsubstituted or substituted in the phenyl ring by one to three radicals from the group comprising halogen, $C_1$-$C_4$-alkyl, trifluoromethyl, $C_1$-$C_4$-alkoxy, nitro, ($C_1$-$C_4$-alkoxy)carbonyl, mono and di-($C_1$-$C_4$-alkylamino)-carbonyl or $C_2$-$C_3$-alkanoyl.

4. The compound claimed in claim 1, wherein:
$R^2$ is nitrophenyl or nitrophenyl substituted by one or two halogen, nitro, $C_1$-$C_4$-alkyl, $C_1$-$C_4$-haloalkyl or $C_1$-$C_4$-alkylsulfonyl groups.

5. The compound claimed in claim 1, wherein:
$R^2$ is nitrophenyl substituted by one chlorine, methanesulfonyl or trifluoromethyl.

6. The compound claimed in claim 1, wherein:
$R^2$ is 2-nitrophenyl substituted by one chlorine, methanesulfonyl or trifluoromethyl.

7. The compound claimed in claim 2, wherein:
$R^2$ is 2-nitrophenyl or 2-nitrophenyl substituted by one or two halogen, nitro, $C_1$-$C_4$-alkyl, $C_1$-$C_4$-haloalkyl and $C_1$-$C_4$-alkylsulfonyl groups.

8. The compound claimed in claim 3, wherein:
$R^2$ is nitrophenyl substituted by one chlorine, methanesulfonyl or trifluoromethyl.

9. The compound claimed in claim 3, wherein:
$R^2$ is 2-nitrophenyl substituted by one chlorine, methanesulfonyl or trifluoromethyl.

10. The compound claimed in claim 1, wherein the $R^3$ radicals, independent of one another, are H or methyl, and n is an integer from 0 to 4.

11. The compound claimed in claim 1, which is a compound of the formula I

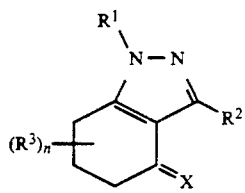

12. The compound claimed in claim 1, wherein X is oxygen.

13. The compound claimed in claim 1, wherein n is an integer from 0 to 3.

14. The compound claimed in claim 9, wherein the $R^3$ radicals, independent of one another, are H or methyl, and n is an integer from 0 to 3, and X is oxygen.

15. A herbicidal composition comprising a herbicidally effective amount of a compound of the formula I or I'

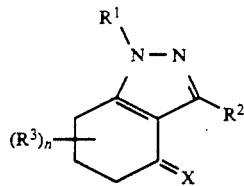

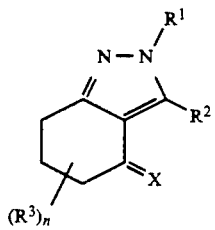

in which:
X is oxygen or sulfur;
$R^1$ is H, $C_1$-$C_6$-alkyl, $C_2$-$C_6$-alkenyl, $C_2$-$C_6$-alkynyl, $C_1$-$C_6$-haloalkyl, ($C_1$-$C_4$-alkoxy)-$C_1$-$C_4$-alkyl, ($C_1$-$C_6$-alkoxy)carbonyl, aryloxycarbonyl, ($C_1$-$C_6$-alkyl)aminocarbonyl, arylaminocarbonyl, phenyl, substituted phenyl or acyl;
$R^2$ is nitrophenyl or nitrophenyl substituted by one or two halogen, nitro, $C_1$-$C_4$-alkyl, $C_1$-$C_4$-haloalkyl and $C_1$-$C_4$-alkylsulfonyl groups;
$R^3$ independent of each of the other $R^3$ radicals is H or $C_1$-$C_5$-alkyl; and
n is an integer from 0 to 6; and with the exception of 4,5,6,7-tetrahydro-4-oxo-1,6,6-trimethyl-3(4-nitrophenyl)1H-indazole and customary formulation auxiliaries.

16. A method for selectively controlling harmful plants, which comprises applying an effective amount of a compound of the formula I or I' as defined in claim 15 to the plants, seeds of plants, or to the area under cultivation.

17. The method claimed in claim 16, wherein:
$R^2$ is 2-nitrophenyl or 2-nitrophenyl substituted by one or two halogen, nitro, $C_1$-$C_4$-alkyl, $C_1$-$C_4$-haloalkyl and $C_1$-$C_4$-alkylsulfonyl groups.

18. The method claimed in claim 16, wherein:
$R^2$ is 2-nitrophenyl substituted by one chlorine, methanesulfonyl or trifluoromethyl.

19. The method claimed in claim 16, wherein the $R^3$ radicals, independent of one another, are H or methyl, and n is an integer from 0 to 3, and X is oxygen.

* * * * *